(12) United States Patent  
Hibler

(10) Patent No.: US 7,105,007 B2
(45) Date of Patent: Sep. 12, 2006

(54) CERVICAL MEDICAL DEVICE, SYSTEM AND METHOD

(76) Inventor: Timothy B. Hibler, 4386 Hale Ranch La., Fair Oaks, CA (US) 95628

( * ) Notice: Subject to any disclaimer, the term of this patent is extended or adjusted under 35 U.S.C. 154(b) by 19 days.

(21) Appl. No.: 10/719,500

(22) Filed: Nov. 21, 2003

(65) Prior Publication Data

US 2004/0122463 A1    Jun. 24, 2004

Related U.S. Application Data

(60) Provisional application No. 60/428,397, filed on Nov. 21, 2002.

(51) Int. Cl.
*A61M 29/00* (2006.01)

(52) U.S. Cl. .................. 606/193; 606/194; 606/196; 606/197

(58) Field of Classification Search ............ 606/192, 606/193, 197, 198, 194, 196
See application file for complete search history.

(56) References Cited

U.S. PATENT DOCUMENTS

| 2,687,131 | A | * | 8/1954 | Raiche .............. 604/101.05 |
| 3,848,602 | A | * | 11/1974 | Gutnick .............. 606/193 |
| 4,018,230 | A | | 4/1977 | Ochiai et al. |
| 4,137,922 | A | | 2/1979 | Leininger et al. |
| 4,168,709 | A | | 9/1979 | Bentov |
| 4,228,801 | A | | 10/1980 | Magnasco et al. |
| 4,237,893 | A | | 12/1980 | Michaels |
| 4,430,076 | A | * | 2/1984 | Harris .............. 604/103.03 |
| 4,555,242 | A | * | 11/1985 | Saudagar .............. 604/103.08 |
| 4,664,114 | A | | 5/1987 | Ghodsian |
| 4,686,985 | A | * | 8/1987 | Lottick .............. 606/192 |
| 4,836,204 | A | * | 6/1989 | Landymore et al. ......... 606/215 |
| 4,976,692 | A | * | 12/1990 | Atad .............. 604/101.03 |
| 5,163,906 | A | * | 11/1992 | Ahmadi .............. 604/101.03 |
| 5,947,991 | A | * | 9/1999 | Cowan .............. 606/191 |
| 5,954,740 | A | | 9/1999 | Ravenscroft et al. |
| 6,398,792 | B1 | | 6/2002 | O'Connor |
| 2002/0013601 | A1 | * | 1/2002 | Nobles et al. .............. 606/193 |

* cited by examiner

*Primary Examiner*—Gary Jackson
*Assistant Examiner*—Michael G. Mendoza
(74) *Attorney, Agent, or Firm*—K. David Crockett, Esq.; Crockett & Crockett

(57) ABSTRACT

A device and method for dilating a cervical canal. The device includes an elongated member with an expandable anchoring component attached to its distal tip. An expandable dilating member is attached to the elongated member proximally of the anchoring component for dilating the cervical canal. The anchoring component can be expanded after insertion of the device into the cervical canal to correctly position the device relative to the canal. A device and method for sealing a cervical canal is also provided. The device includes a tube having an expandable seal assembly attached to its distal end. The seal assembly has a ridged or corrugated surface when it is in an expanded condition to provide a seal for the cervical canal.

5 Claims, 6 Drawing Sheets

CERVICAL MEDICAL DEVICE, SYSTEM AND METHOD

REFERENCE TO PROVISIONAL APPLICATION

This application claims priority to U.S. Provisional Application No. 60/428,397, which was filed on Nov. 21, 2002.

BACKGROUND OF THE INVENTION

1. Field of the Invention

The present invention relates to medical devices, systems, and methods for dilating a cervical canal in a female patient.

2. Description of the Related Art

The cervix is a dense yet distendible organ that responds to internal pressure (within the endocervical canal) by expanding within anatomical limits to assume the diameter or shape of the item causing the pressure. If this pressure is applied gradually, the tissues of the cervix will usually experience minimal damage. It has been observed that if the pressure is maintained for a short period of time, the cervix will temporarily fix itself to that diameter. In other words, the cervix will temporarily stay open even after the pressure has been removed. It will then gradually return to its normal resting diameter of about 3–4 mm.

Since the early 1800s physicians have been attempting to visualize the endometrial cavity through the endocervical canal using a variety of optical instruments. In the late 1800s, Pantaleoni removed a uterine polyp and used silver nitrate to control the bleeding, thereby completing the first successful procedure done through a hysteroscope.

Hysteroscopy, both diagnostic and operative, has come a long way since then, but the fundamental challenges of hysteroscopy have remained unchanged. The two most basic challenges of hysteroscopy are: (1) dilating or opening the cervix in order to permit the insertion of the instrument of choice; and (2) distending the uterine cavity with some form of gas or liquid in order to see and operate.

The first challenge has been addressed in two ways. The first is a series of mechanical dilators that are, for the most part, blunt tipped, tapered metal or plastic rods that are offered in a graduated set of increasing diameters. The mechanical dilators are gently inserted into the cervix starting with the smallest and moving through the larger sizes until the cervix is opened to the desired diameter. Unfortunately, this method can be painful for the patient and often results in tearing of the cervical tissues, which causes bleeding and frequently leads to unintentional perforation of the uterine wall.

Gynecologists recognized the benefits of a more gradual dilation of the cervix and two additional methods were pursued. The first is a seaweed based product called Laminaria and the second is a prostaglandin based drug called Misoprostol also known as Cytotec®, which is manufactured by Pfizer, Inc.

Laminaria is a very thin piece of seaweed that is inserted into the endocervical canal. As the Laminaria absorbs tissue fluid from the body, it swells gradually and dilates the cervix in the process. This method has the benefit of eliminating the pain associated with mechanical dilation and allows the operator to avoid or use minimal mechanical dilation. The problems associated with Laminaria are that it requires an additional visit to the doctor because the medical procedure to be performed must be done between 12 and 24 hours after the insertion of the Laminaria and there is no control of the final dilated diameter of the cervix.

Misoprostol is a drug that has a softening effect of the cervical tissues, allowing cervical dilation with less force. It can be administered either orally or through the vagina. In either case, the patient can administer the drug herself but it does require a trip to the pharmacy. There are however inconveniences associated with the use of Misoprostol. In the case of self-administration, it requires the compliance of the patient and a prescription, and the patient must pick up the prescription from the pharmacy. Since it is a form of prostaglandin, it may also contribute to uterine cramping, which causes pain and discomfort. If the cervix become too soft, establishing a seal on the hysteroscope on the day of the procedure may be problematic. Like all drugs, there can be numerous side effects and complications associated with the use of Misoprostol.

The second and simultaneous effort to address the first challenge of hysteroscopy is to make the instruments smaller, thus requiring a smaller opening of the cervix. This solution does indeed reduce the difficulties and complications mentioned above, but at the cost of a reduction in visual clarity. Additionally, the small instruments that are required for these smaller hysteroscopes are inadequate for all but the most basic procedures a gynecologist performs. These smaller scopes are thus restricted to limited visual diagnostic procedures only.

Since the uterus is only a potential cavity, it needs to be distended in order to see into it, which is the reason for the second basic hysteroscopic challenge. The two primary methods of distension have been and remain to this day to pump gas (usually carbon dioxide) and a fluid of some kind into the uterus. There have been many fluids used for uterine distension over the years, such as physiologic saline, 5% dextrose in water, glycine, sorbitol and others. Each of these solutions and gases carry certain benefits and complications.

All of these distension media do provide at least one common challenge to the hysteroscopist: the need to contain them within the confines of the uterine cavity such that a slight positive intrauterine pressure is established. It is this containment and resultant positive pressure that distends the walls of the uterine cavity, permitting visualization and procedural manipulation by the physician. Typically, the distension media escape past the hysteroscope down the endocervical canal and into the vagina. This loss of fluid not only makes establishing and maintaining a positive pressure difficult, it also allows for a fairly significant volume of contaminated fluid to flow onto the operating room floor. The flow of fluid onto the operation room floor represents a safety hazard for the operating room personnel and if the fluid being used is a non-electrolyte, it also poses a safety risk to the patient. In the latter case, if enough non-electrolytic fluid is absorbed by the patient, it can cause a condition known as hyponatremia, which has a morbidity and mortality risk associated with it. In order to avoid fluid overload, the operating room personnel must carefully monitor how much fluid is introduced into the patient versus how much is recovered, with the net difference assumed to have been absorbed. If fluid is lost to the drapes, floor, etc. this task becomes more difficult and less accurate.

SUMMARY OF THE INVENTION

According to one aspect of the present invention, a cervical medical device is provided. The device has an elongated member sized to be inserted into an undilated cervical canal. An expandable mechanism is attached to the elongated member. The device also has an anchoring feature to anchor the device within the cervical canal.

According to another aspect, a cervical anchoring method is provided. A hollow tube is inserted into a cervical canal. At least one expandable dilator is also inserted into the cervical canal. The at least one expandable dilator is then radially expanded within the canal to dilate the cervical canal while the tube is in the canal.

According to another aspect, a cervical dilating device is provided. The dilating device has an elongated member having a proximal end and a distal end. A first expandable component is attached to the distal end of the elongated member. A second expandable component is attached to the elongated member proximally of the first expandable component. In an illustrated embodiment, the device also has a lumen running through the entire length of the device. An expansion mechanism is preferably coupled to the first and second expandable components to expand the expandable components.

According to another aspect, a cervical sealing device is provided. The cervical sealing device has an elongated member having a proximal end and a distal end. An expandable seal assembly is attached to the distal end of the elongated member. The seal assembly has an uneven surface when it is in an expanded condition.

According to yet another aspect of the invention, a method of dilating a cervical canal is provided. A dilating device is inserted into the cervical canal. The dilating device includes an elongated member having a first expandable component attached to the distal end of the elongated member. A second expandable component is attached to the elongated member proximally of the first expandable component. The first expandable component is expanded after the device is inserted into the cervical canal. The device is then retracted until resistance is felt and the second expandable component is expanded to dilate the cervical canal.

According to another aspect, a method of sealing a cervical canal is provided. A sealing device is introduced into the cervical canal. The device includes a tube and an expandable seal assembly attached to a distal end of the tube. The seal assembly has an even surface when it is expanded. The seal assembly is expanded after the device is introduced into the canal. The device may comprise an expansion mechanism coupled to the seal assembly.

According to yet another aspect, a method of providing a seal for a cervical canal is provided. A cervical sealing device is inserted into the cervical canal. The device includes a cannula having a plurality of valves. An inflatable balloon is attached to a distal end of the cannula, wherein the balloon has an uneven surface when inflated. The balloon is then inflated after the device is inserted into the cervical canal to seal the canal.

BRIEF DESCRIPTION OF THE DRAWINGS

These and other aspects of the invention will be readily apparent to the skilled artisan in view of the description below, the appended claims, and from the drawings, which are intended to illustrate and not to limit the invention, and wherein:

DETAILED DESCRIPTION OF THE PREFERRED EMBODIMENT

The following detailed description of the preferred embodiments presents a description of certain specific embodiments to assist in understanding the claims. However, one may practice the present invention in a multitude of different embodiments as defined and covered by the claims.

Referring more specifically to the drawings for illustrative purposes, the present invention is embodied in the devices generally shown in the Figures. It will be appreciated that the devices may vary as to configuration and as to details of the parts, and that the methods may vary as to the specific steps and sequence, without departing from the basic concepts as disclosed herein.

Figure 1A:
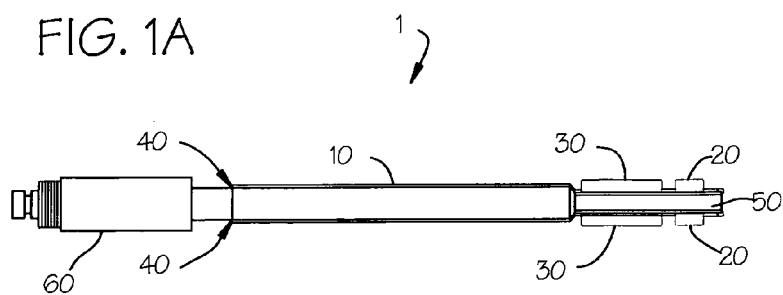
FIGS. 1A–1C show various schematic views of an embodiment having a distal anchor and a dilating member.
Figure 1B:
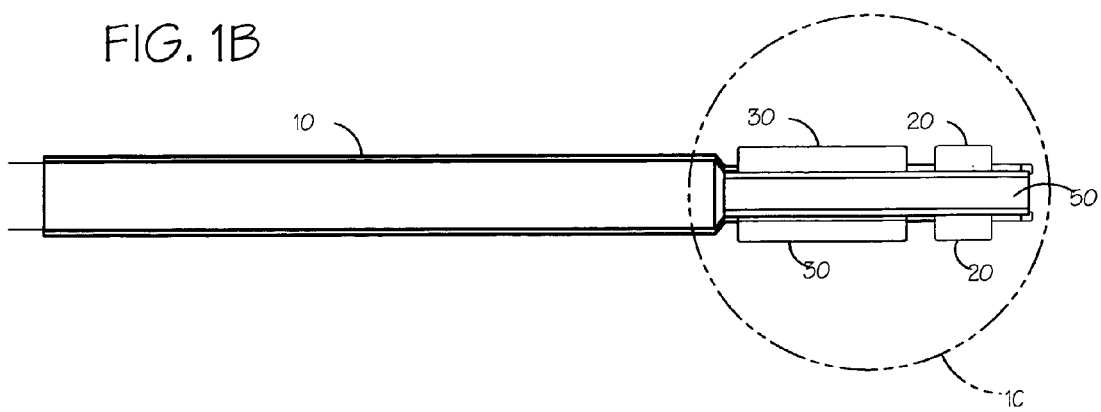
Figure 1C:
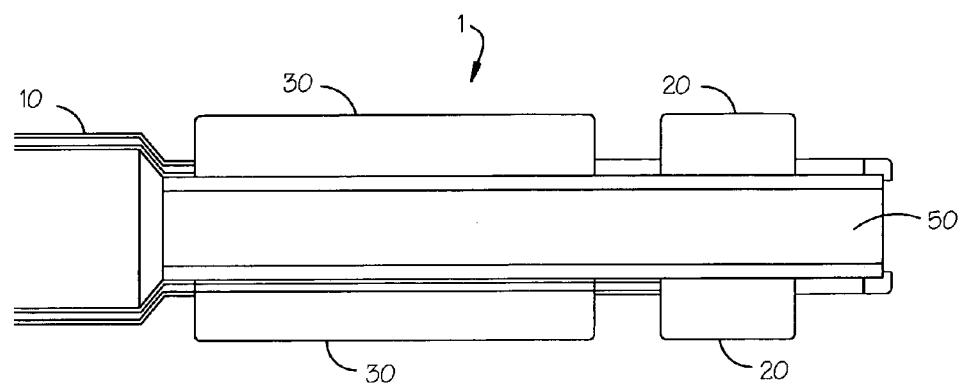

One embodiment of the invention is illustrated by reference to FIGS. 1A–1D. As shown in FIGS. 1A–1C, the device 1 has an elongated member 10 having a proximal end and a distal end. Preferably, the elongated member 10 is a slender, rod-like instrument. The elongated member 10 preferably is about 15–30 cm long and has a diameter no greater than about 3 mm. In a preferred embodiment, the elongated member 10 has a central lumen 50 running along the length of the device 1. The skilled artisan will appreciate that, in some embodiments, the elongated member 10 may have a length substantially corresponding to the length of the cervical canal.

With reference to FIG. 1A, a distal anchor 20 is positioned along the distal end portion of the elongated member 10, at or adjacent to the distal tip of the elongated member 10. A dilating member 30 is also positioned along the distal end portion of the elongated member 10 proximally of the distal anchor 20, as shown in FIGS. 1A–1D.

The distal anchor 20 preferably is an expandable member. According to one embodiment, the distal anchor 20 comprises an expandable member that is adjustable between radially collapsed and radially expanded conditions. As shown in FIG. 1A, the distal anchor 20 is in a radially expanded condition. In the radially collapsed condition, the expandable member may be delivered to the anchoring location of the cervical canal, as will be more fully described below with reference to FIGS. 2A–2F. Once the distal anchor 20 is positioned at the anchoring location, the distal member 20 may be expanded to the radially expanded condition. The distal anchor 20 in the radially expanded condition preferably has an expanded outer diameter that is greater than the initial inner diameter of the cervical canal at the anchoring location such that the expandable distal anchor 20 is adapted to radially engage the wall of the cervical canal at the juncture of the cervical canal and the endometrial cavity to anchor thereto. With the distal anchor 20 anchored at the anchoring location, the dilating member 30 may be expanded within the cervical canal to dilate the cervical canal from an initial inner diameter to a dilated inner diameter that is greater than the initial inner diameter of the cervical canal.

Figure 1D:
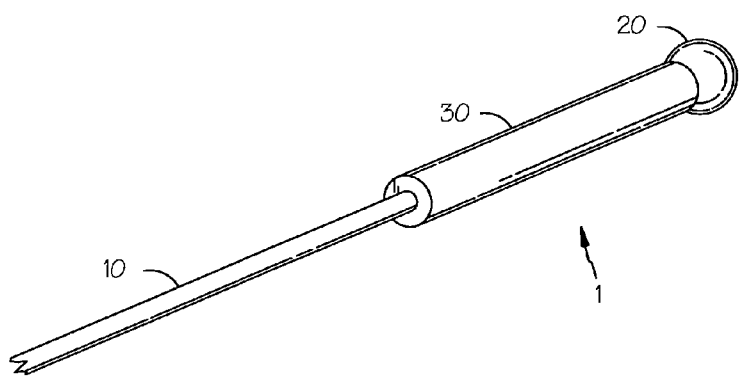
FIG. 1D is a perspective view of an embodiment of the device.

In a preferred embodiment, the distal anchor 20 is a rounded balloon, as shown in FIG. 1D. Preferably, the distal anchor 20 has a diameter no greater than about 5 mm. The distal anchor 20 may be expanded, or inflated, after it is inserted into the endometrial cavity. The device 1 may then be gently pulled back until resistance is felt, establishing that the tip of the device 1 is very close to the internal cervical os. This action is similar to inserting a Foley balloon catheter into the urinary bladder. According to an alternative embodiment of the device 1, the skilled artisan will appreciate that the distal anchor 20 is a small deployable umbrella-like device that can be used to determine positioning of the device 1 relative to the internal cervical os in a similar fashion to the method described above.

According to another embodiment, the device 1 has an optical imaging component instead of the distal anchor 20. The optical imaging component may be, for example, an imaging fiber. The optical imaging component resides in the central lumen 50 of the elongated member 10 and allows the operator to visually confirm the position of the distal tip of the device 1 before expanding the dilating member 30. Those skilled in the art will appreciate that the optical imaging component may be provided in addition to the distal anchor 20 as well.

According to an embodiment, the dilating member 30 comprises an expandable member that is also adjustable between a radially collapsed condition and a radially expanded condition. Preferably, the expandable dilating member 30 in the expanded condition has a working length substantially corresponding to the length of the cervical canal, and has an expanded outer diameter that is greater than the initial inner diameter of the cervical canal. The dilating member 30 may be inserted into the cervical canal proximally adjacent to the anchoring location so as to substantially engage and dilate the cervical canal wall to the desired dilated inner diameter.

In a preferred embodiment, the dilating member 30 is an inflatable balloon that can be used as a dilator for the cervical canal wall, as shown in FIGS. 1A–1C. More preferably, the balloon is cylindrical, as shown in FIGS. 1A–1D. The dilating member 30 shown in FIGS. 1A–1D is in its inflated condition. The length of the balloon 30 in its inflated condition is preferably between 40 mm and 100 mm, and more preferably about 60 mm. The overall diameter of the balloon 30 in its inflated condition is preferably between 5 mm and 20 mm, and more preferably about 8 mm.

The overall diameter of the deflated balloon 30 is preferably less than 3.5 mm, and more preferably less than about 3 mm because the endocervical canal has a normal resting diameter of about 3–4 mm. If the dilating member 30 is preferably less than 3 mm in diameter in its collapsed position, there will be less force for the initial insertion into the cervical canal, which will provide more control for the operator and a reduction in tearing of cervical tissue and inadvertent perforations of the uterine wall.

The balloon 30 may be attached to the distal end portion of the elongated member 10. The balloon 30 may be inserted into the endocervical canal and is then inflated in order to dilate the canal to a predetermined diameter. A skilled artisan will appreciate that in another embodiment, the device 1 does not have a distal anchor 20 and may be used to dilate the cervical canal with only the dilating member 30 attached to the elongated member 10.

Figure 2A:
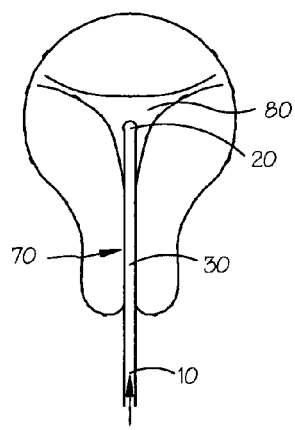
FIGS. 2A–2F show a method of dilating a cervical canal.
Figure 2B:
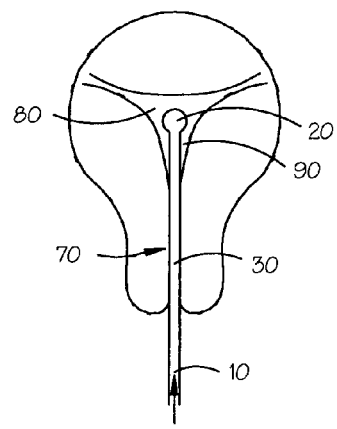
Figure 2C:
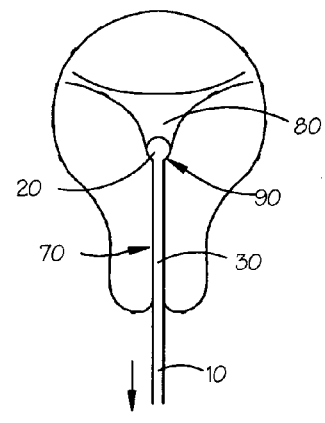

FIGS. 2A–2F show a method of using an embodiment of the device 1 to dilate the cervical canal. The embodiment shown in FIGS. 2A–2F has both a distal anchor 20 and a dilating member 30. As shown in FIG. 2A, the device 1 is inserted into the endocervical canal 70. FIG. 2B shows the distal anchor 20 being inflated, preferably with a fluid-filled syringe, in the endometrial cavity 80. As shown in FIG. 2C, the device 1 may then be retracted until the resistance of the distal anchor 20 against the internal cervical os 90 is felt. In this position, the device 1 is properly positioned in the canal in its anchoring location.

Figure 2D:
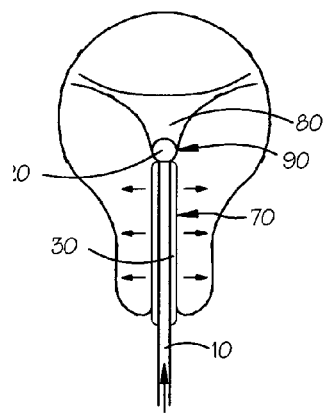

Once the device 1 is in the anchoring location, the dilating member 30 may be expanded preferably with gradually increasing pressure from a fluid filled syringe until the maximum volume of the dilating member 30 is reached, as shown in FIG. 2D. The skilled artisan will appreciate that the distal anchor 20 and the dilating member may be inflated by other methods as well.

In a preferred embodiment, the expandable members of the distal anchor 20 and dilating member 30 are independently inflatable. Those skilled in the art will understand that there is a choice of inflation mechanisms for the distal anchor 20 and the dilating member 30. According to one embodiment, the operator may manually inflate the distal anchor 20 and/or the dilating member 30 with a syringe or a syringe-like device. In certain embodiments, the syringe may be filled with liquid. Other expandable materials, including but not limited to gases and expandable foams and plastics, may be used to inflate the distal anchor 20 and the dilating member 30 as well. A skilled artisan will appreciate that the distal anchor 20 and dilating member 30 may also be expanded by means of mechanical or chemical expansion.

According to yet another embodiment, the device 1 further includes an automated expansion system that is coupled to the expandable dilating member 30. The automated expansion system gradually expands the dilating member 30 to the expanded condition over a longer period of time, such that tissue trauma and pain of the dilation is reduced. In yet another embodiment, the automated expansion system comprises a monitoring assembly and a control assembly. The monitoring assembly monitors the value of a predetermined parameter related to the expansion of the dilating member 30, and the control assembly controls expansion of the dilating member 30 according to the monitored value. In one embodiment, the control assembly can stop expansion of the dilating member 30 upon the value or the parameter meeting a predetermined set point. According to another embodiment, the set point is not predetermined but rather calculated based on one or more other monitored or otherwise observed parameters related to the patient (e.g., initial inner diameter of the cervical canal or other anatomical considerations). In yet another embodiment, the gradual expansion of the dilating member 30 is controlled at a set rate (e.g., volume/unit time) until either a predetermined or calculated value, such as volume, diameter, or time, is met. In still another embodiment, the gradual expansion of the dilating member 30 is controlled to terminate at a constant end diameter value based on a measured resistance at the cervical canal wall to expansion (i.e., pressure required to change). Specified parameters may include actual values, such as pressure, volume, time, diameter, etc., or rates of change thereof, or combinations of any of the foregoing. According to yet another embodiment, the expansion of the expandable dilating member 30 is controlled manually by a healthcare provider.

Figure 2E:
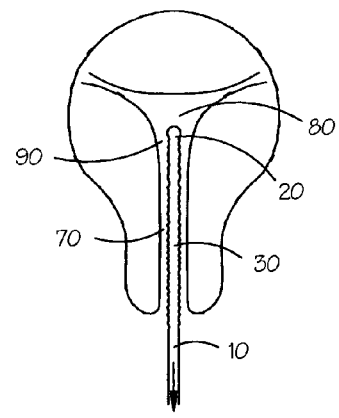
Figure 2F:
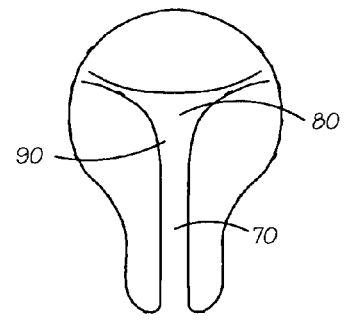

The dilating member 30 may be allowed to remain at its full volume for a time period to dilate the cervical canal. As shown in FIG. 2E, both the distal anchor 20 and the dilating member 30 may then be deflated to remove the device 1 from the cervical canal. At this point, the cervical canal remains dilated, as shown in FIG. 2F, and a hysteroscopic or other intrauterine device can then be inserted into the uterus before the cervix relaxes down to its natural resting diameter.

Another embodiment provides for a collapsed, mesh-like guide tube that may be introduced on a flexible introducer into the endocervical canal. Introducer may then removed from the endocervical canal and the mesh guide tube remains in place in the canal. The mesh guide tube is preferably formed from a synthetic plastic material and about 3–3.5 mm in diameter. A dilating device, including but not limited to the device 1, or a series of successively larger dilating devices where each subsequent dilating device has a larger diameter, may then be introduced into the canal through the mesh guide tube to gradually dilate the canal.

Those skilled in the art will appreciate that various expandable materials may be used to form the balloons 20, 30 and other structural components of the device 1. Preferably, the balloons 20, 30 are rigid-walled balloons formed from polyethylene terephthalate (PET). A skilled artisan will appreciate that other materials, including but not limited to nylon or silicon, may be used for the balloons 20, 30 as well. The features shown in FIGS. 1A–1C may be modified with suitable substitutes, such as, for example, replacing inflatable balloons with other expandable members, such as expandable cages, expanding foam, expanding chemical materials and the like, as would be apparent to one skilled in the art.

According to yet another embodiment, the elongated member 10 of the device 1 is not hollow and is used only for dilation purposes. Accordingly, the skilled artisan will understand that the device 1 design may be simplified and profiles may be minimized to allow atraumatic passage of the device 1 into an undilated cervical canal and still allow for the controlled dilation of the cervical canal.

The device 1 may be used as a stand-alone cervical canal dilator device that can be subsequently removed for later procedures to be performed with other medical devices. In a preferred embodiment, the proximal end of the device 1 may also be positioned, or slid, over the distal end portion of another medical device 60 (such as a hysteroscopic or intrauterine device), as shown in FIG. 1A. The proximal end of the elongated member 10 is preferably coupled to the distal end portion of a hysteroscopic or intrauterine device 60 with ports adapted to couple to at least one inflation device to inflate each of the balloons 20, 30, as schematically shown by arrows 40 in FIG. 1A. In the case of coaxial use of the device 1 over another device through the lumen 50, a stop area may be provided on the elongated member 10 to abut the tip of the other device 60 for coupling the device 1 to the other device 60.

Accordingly, existing intrauterine treatment or diagnostic devices may be modified by use of the embodiments of the present invention to allow for dilation of and/or sealing of the cervical wall. The skilled artisan will appreciate that the device 1 may be preloaded onto an internal treatment device and inserted together. Dilation of the cervical canal and sealing against fluid leakage from the uterus may be achieved using the device 1.

The invention, according to another aspect, includes a medical device system and method that may be positioned within a cervical canal, allow passage of fluids into the uterus through the cervical canal, and also provide a substantial seal against flow of pressurized fluids from within the uterus and outward through the cervical canal. In some embodiments, the device is an integral component to various hysteroscopic devices that require some form of fluid or gas containment and control during hysteroscopic or intrauterine procedures.

The device includes a cervical sealing/anchoring expandable element, such as a balloon that is designed to work in conjunction with hysteroscopic or other intrauterine devices. When the balloon is positioned over a hysteroscopic or intrauterine device and the device is inserted into the uterus, the balloon, or other expandable element, is inflated, or otherwise expanded, thereby creating a seal between the device and the wall of the endocervical canal, as will be more fully described below. The expandable element may be either curved or straight.

According to another aspect of the invention, the system includes a transcervical treatment device assembly with the device, which comprises an elongated body having a proximal end portion and a distal end portion. The treatment assembly and seal assembly are disposed at least in part along the distal end portion. The distal end portion is adapted to be positioned at least in part within the cervical canal with the proximal end portion located externally of the body proximally of the vagina. The treatment assembly along the distal end portion is configured for use in performing a medical procedure within the female reproductive system, such as within the uterus or fallopian tubes. The seal assembly, also along the distal end portion, substantially seals against flow of pressurized fluid from within the uterus and outward from the body though the cervical canal.

Figure 3A:
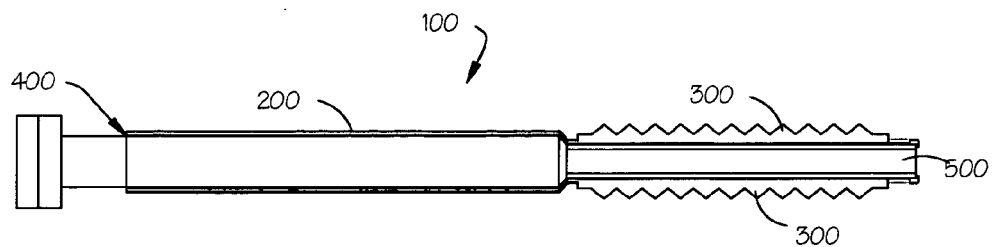
FIGS. 3A–3B show two schematic views of another embodiment having a seal assembly over an intrauterine treatment device.
Figure 3B:
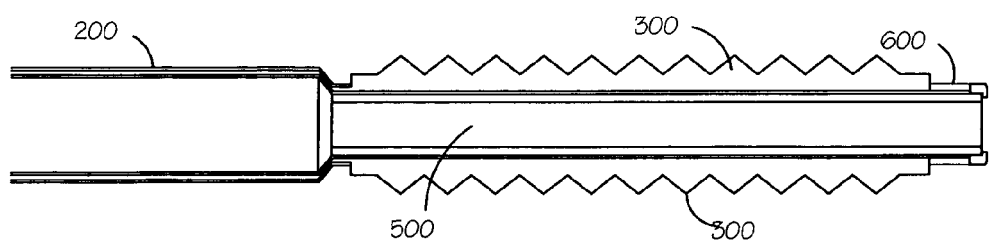

FIGS. 3A and 3B illustrate an embodiment of the invention, which provides a cervical sealing device 100 that is adapted to seal a cervical canal against leakage of pressurized fluid from the uterus during use with an internal device delivering such fluids into the uterus. In one embodiment shown in FIGS. 3A and 3B, the device 100 comprises an elongated body 200 having a proximal end portion, a distal end portion, and a lumen 500 extending through the entire length of the device 100.

The cervical sealing device 100 in the embodiment shown in FIGS. 3A and 3B is configured to fit over an outer surface of another medical device, such as, for example, an interuterine fluid delivery device. Preferably, the lumen 500 is configured to fit around and engage an outer surface along the distal end portion of an intrauterine treatment device.

A distal stop region 600 is preferably provided at the distal tip of the device 100, as shown in FIG. 3B. The distal stop region 600 is positioned at the distal tip of the lumen 500. The distal stop region 600 allows precise placement of a seal assembly 300 relative to the lumen 500 and keeps the seal assembly 300 from sliding along the lumen 500.

The seal assembly 300 is located along the distal end portion of the elongated body 200. The seal assembly 300 provides a seal against the outward flow of pressurized fluids from within the uterus and externally around the cervical sealing device 100. The seal assembly of the illustrated embodiment, shown in FIGS. 3A and 3B, is a corrugated inflatable balloon, which provides for regions of increased expansion, separated by regions of relatively decreased expansion when inflated. In this embodiment, the balloon is adjustable between a radially collapsed condition for delivery into the cervical canal and a radially expanded condition that radially engages the inner wall of the cervical canal to effect the seal. In a preferred embodiment, the balloon 30 has 3–4 ridges. The ridges of the balloon provide for a "keyway" effect along an engaged cervical canal wall, helping to secure or anchor the seal assembly 300 in place during pressurization of the distal uterus, and also helps to prevent leakage of pressurized interuterine fluid. It will be understood that the pressure points are anchoring features created by the regions of increased expansion provide a seal for the cervical canal.

A skilled artisan will appreciate that other substitute seal members may be used, such as, for example, a series of discrete balloons or other expandable structures, such as cages or the like. In a preferred embodiment, the seal assembly 300 comprises a plurality of expandable members located that are spaced in series along a length of the distal end portion of the elongated body 200 (see FIG. 4 and attendant text). In one embodiment, the aggregate length of the expandable members corresponds to a substantial portion of the length of the cervical canal. Such spaced expandable members provide a "keyway" effect along a cervical wall with a series of dilated regions separated by regions less dilated, or in some cases the areas of separation may not be dilated at all.

Preferably, the outer diameter of the device 100 along the region of the seal assembly 300 is increased by at least about 2 millimeters when the seal assembly 300 is activated or expanded to seal against fluid flow from the uterus. More preferably, the outer diameter of the device along the seal assembly 300 region is increased by between about 3 and about 4 millimeters during the sealing mode of use.

The inflatable balloon or balloons 300 are preferably coupled to an inflation source, shown schematically by way of an arrow 400 in FIG. 3A. Those skilled in the art will understand that the inflation source may be coupled to seal assembly 300 at any point and that various inflation sources, such as the ones described above, may be used to expand the seal assembly 300. The seal assembly preferably has a length between 40 mm and 100 mm, and more preferably about 60 mm. In one embodiment, the seal assembly 300 engages the cervical wall along the entire effective length of the cervical wall.

It is important to note that the dilation of the cervix in response to pressure actually causes a reduction in that pressure. Furthermore, the endocervical canal does not dilate uniformly. It only dilates where pressure is applied. Thus, one can dilate one area of the endocervical canal without increasing the diameter of the rest of the canal.

Figure 4:
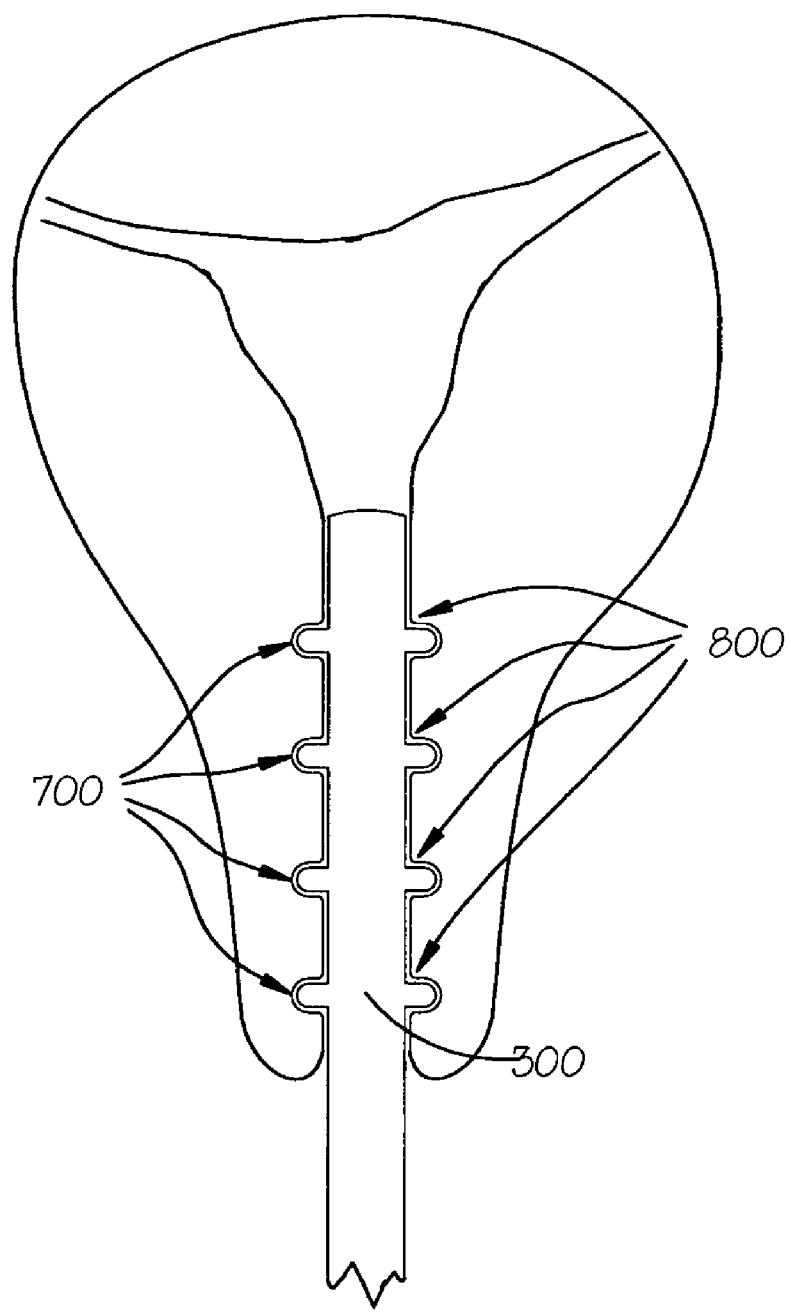
FIG. 4 is a view of an embodiment used to dilate and seal the cervical canal.

Another embodiment will be described with reference to FIG. 4. The seal assembly 300 is preferably designed to create one or more pressure points 700. Preferably, these pressure 700 points are narrow, annular pressure points along the length of the cervical canal. Alternatively, the seal assembly may be dimpled to create the pressure points. In a preferred embodiment shown in FIG. 4, the seal assembly 300 is a balloon shaped such that when it is inflated, it assumes a shape that resembles several, evenly spaced annular donuts or rings on a pole that runs through the donut holes, as shown in FIG. 4. The area where the donut or ring contacts the wall of the cervical canal is a higher pressure point 700, and the spaces between the donuts or rings are lower pressure points 800.

The illustrated seal assembly 300 works as a seal because it has increased surface contact with the endocervical canal and creates several distinct "dams" due to a slightly higher pressure in the area 700 of the donut or ring relative to the adjacent low pressure bands 800. These "dams" will prevent fluid or gas loss from the uterus through the cervical canal.

In addition to fluid and gas control, the cervical seal assembly 300 of FIG. 4 also acts as an anchor because of the alternating areas of high and low pressure corresponding to the annular rings 700 and spaces 800 along the length of the balloon 300. The cervix will dilate to the shape of the balloon 300 when the balloon 300 is inflated in the endocervical canal, as shown in FIG. 4. The spaces of lower pressure 800 between the rings create areas of the cervical canal that are not dilated as much as the areas 700 corresponding to the annular rings. As these less-dilated areas 800 have a smaller diameter than the balloon's rings, the seal assembly 300 cannot be moved without first dilating these narrower bands of the cervical canal.

Since, in the preferred embodiment, there are several rings, the coefficient of friction is quite high and an anchoring effect results. Thus, the seal assembly 300 also provides an increased coefficient of friction between the hysteroscopic device and the walls of the endocervical canal. This increase coefficient of friction stabilizes the position of the device 100 relative to the endocervical canal, and further minimizes any inadvertent extraction of the device 100 or a change in position of the device 100 inwardly or outwardly that might result in an undesirable result. If the operator of the device 100 needs to reposition the device 100, the balloon 300 is preferably deflated to reposition the device 100 before the balloon 300 is reinflated (provided it is safe to do so). As with previously described embodiments, it will be understood that the seal assembly of FIG. 4 can be a balloon, as illustrated, or other expandable element.

Figure 5A:
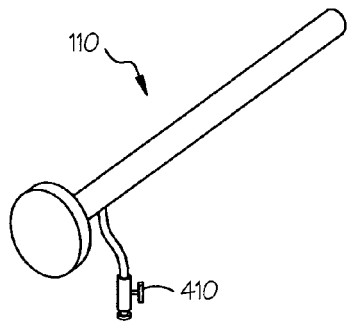
FIGS. 5A–5D show perspective views of an alternative embodiment.
Figure 5B:
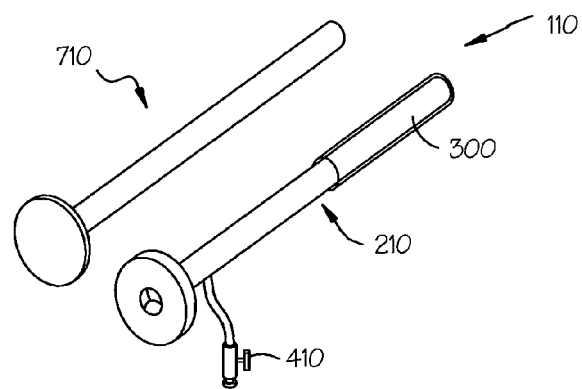

In an embodiment shown in FIGS. 5A–5D, the device 110 permits independent movement of a hysteroscopic or other intrauterine device relative to the device 110 itself. FIG. 5A is a perspective view of the assembled device 110 prior to insertion into the endocervical canal. FIG. 5B shows an exploded view of the device 110, which comprises an obturator 710 and a rigid-walled cannula 210, which is attached a seal assembly 300, which can be as described above on the distal end of the cannula 210.

Figure 5C:
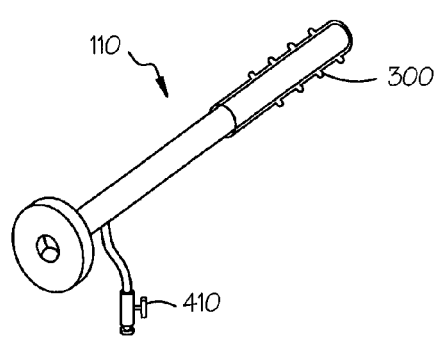

The obturator 710 may be used to insert the cannula 210 into the endocervical canal. The cannula 210 can be either curved or straight and may have an optical imaging component. The seal assembly 300 is attached to the outer surface of the cannula 210. As shown in FIGS. 5A–5C, the cannula 210 also has a valve 410 for use with the illustrated inflatable seal assembly.

Figure 5D:
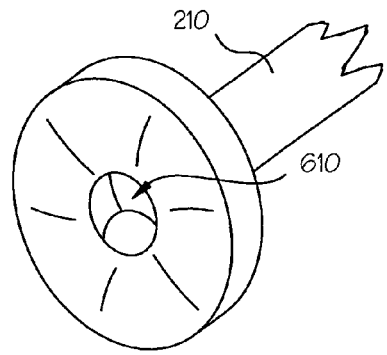

FIG. 5C is a perspective view of the device 110 with the seal assembly 300 expanded after the obturator 710 has been removed. With reference to FIG. 5D, the cannula 210 has an arrangement of diaphragm-shaped seals 610 on its proximal end, which act as a second valve in addition to valve 410. While the seals 610 provide an additional seal, in addition to valve 410, for preventing leakage of fluid or gas through the cervical canal, the seals 610 do allow other devices, such as hysteroscopic or other intrauterine devices to pass through the device 110 and into the endometrial cavity.

The inner diameter of the cannula 210 and its seals 610 preferably corresponds to the outer diameter of a hysteroscopic or intrauterine device that is used with the device 110. The skilled artisan will appreciate that there is enough clearance between the inner diameter of the cannula 210 and the outer diameter of the hysteroscopic or intrauterine device so that the hysteroscopic or intrauterine device can move easily through the device 110. The holes in the seals 610 are slightly smaller than the outer diameter of the hysteroscopic or intrauterine device so that a seal can be established between the devices. Those skilled in the art will understand that this embodiment, when used in conjunction with a hysteroscopic or intrauterine device, functions similarly to a surgical trocar used with a laparoscopic instrument.

It will be understood that the present invention improves the ability to perform medical interventional procedures to the female reproductive system via the cervical canal by providing for one or more of the following benefits: anchoring interventional devices with precise, predictable position relative to the cervical canal os; dilating the cervical canal wall; and sealing the cervical canal against leakage of pressurized fluids from the uterus.

Thus, a wide variety of existing procedures and related devices may benefit by incorporation of or otherwise adjunctive use with the present invention. In one particular regard, hysteroscopy, endometrial ablation, and other intrauterine devices and related methods benefit from the ability to dilate, seal, and/or anchor along the cervical canal in a predictable and reliable manner.

The present invention is highly beneficial and specially adapted for use within the cervical canal. However, it is understood that further modifications or improvements may be made to adapt the various features and embodiments for use in other regions of the body. For example, other procedures benefiting from the ability to anchor a treatment or diagnostic device at a precise location along a lumen, in particular relation to a luminal ostium, would benefit by adjunctive use with such embodiments as herein described. In addition, where other needs exist to controllably dilate a lumen, applications of certain of the embodiments and features for controlled dilation are contemplated. Still further, the ability afforded by certain aspects of the present invention to effectively seal around a treatment device to prevent fluid flow therearound may be useful in other procedures within other body lumens or spaces.

Those skilled in the art may practice the principles of the present invention in other specific forms without departing from its spirit or essential characteristics. Accordingly, the disclosed embodiments of the invention are merely illustrative and do not serve to limit the scope of the invention set forth in the following claims.

What is claimed is:

1. A method of dilating a cervical canal, comprising:
    inserting a dilating device into the cervical canal, the dilating device comprising an elongated member, a first expandable component attached to a distal end of the elongated member, and a second expandable component attached to the elongated member proximally of the first expandable component, wherein the second expandable component has an uneven outer surface;
    expanding the first expandable component;
    retracting the dilating device until resistance is felt while the first expandable component is expanded; and
    expanding the second expandable component in the cervical canal after retracting.

2. The method of claim 1, wherein the device further comprises an expansion mechanism coupled to the first and second expandable components.

3. The method of claim 1, wherein the first and second expandable components are expanded using a fluid-filled syringe coupled to the first and second expandable components.

4. The method of claim 1, wherein the first and second expandable components are expanded using a gas-filled syringe coupled to the first and second expandable components.

5. The method of claim 1, wherein the first and second expandable components are rigidwalled balloons.

* * * * *